(12) United States Patent
Munro, III

(10) Patent No.: US 8,444,544 B1
(45) Date of Patent: May 21, 2013

(54) DEVICE AND METHOD FOR INTENSITY MODULATED BRACHYTHERAPY

(76) Inventor: John J. Munro, III, North Andover, MA (US)

( * ) Notice: Subject to any disclaimer, the term of this patent is extended or adjusted under 35 U.S.C. 154(b) by 600 days.

(21) Appl. No.: 12/584,351

(22) Filed: Sep. 3, 2009

(51) Int. Cl.
*A61N 5/01* (2006.01)
(52) U.S. Cl.
USPC ................................. 600/3; 600/1
(58) Field of Classification Search
USPC .......................................... 600/1–8
See application file for complete search history.

(56) References Cited

U.S. PATENT DOCUMENTS

| | | | | |
|---|---|---|---|---|
| 4,702,228 | A | * | 10/1987 | Russell et al. ............ 600/8 |
| 5,226,430 | A | * | 7/1993 | Spears et al. .............. 128/898 |
| 6,036,631 | A | | 3/2000 | McGrath et al. |
| 6,077,213 | A | | 6/2000 | Ciezki et al. |
| 6,482,142 | B1 | | 11/2002 | Winkler et al. |
| 6,540,655 | B1 | | 4/2003 | Chin et al. |
| 6,575,887 | B1 | * | 6/2003 | Schrayer ................ 600/3 |
| 6,626,816 | B1 | | 9/2003 | Ciezki et al. |
| 7,407,476 | B2 | | 8/2008 | Lubock et al. |
| 7,413,539 | B2 | | 8/2008 | Lubock et al. |
| 2003/0120128 | A1 | * | 6/2003 | Taschereau et al. ........ 600/1 |
| 2005/0261541 | A1 | | 11/2005 | Henderson et al. |
| 2007/0129592 | A1 | * | 6/2007 | Lubock et al. ............ 600/1 |
| 2008/0009659 | A1 | * | 1/2008 | Smith et al. ............. 600/3 |

OTHER PUBLICATIONS

Accelerated Partial Breast Irradiation. Sauer R, Sautter-Bihl ML, Budach W, Feyer P, Harms W, Souchan R, Wollwiener D, Kreienberg R, Wenz F. Cancer. Sep. 15, 2007. vol. 10; 6; pp. 1187-1194.*

Booth TE, et al., Report No. "MCNP-A General Monte Carlo N-Particle Transport Code, Version5" LA-UR-03-1987, 2003 (Cover only).
Chao KK, et al., Analysis of treatment efficacy, cosmesis, and toxicity using the MammoSite breast brachytherapy catheter to deliver accelerated partial-breast irrdaiation: Willima Beaumont Hospital Experience, Int. JK. Radiat. Oncol. Biol. Phys. Sep. 1, 2007; 69(1): 32-40.
Kaufman SA, et al., Long-term outcome and toxicity in a Phase I/II trial using high-dose-rate multicatheter interstitial brachythyerapy for T1/ T2 breast cancer, Brachytherapy. Oct.-Dec. 2007; 6(4): 286-92.
Lin, L., et al., The use of directional interstitial sources to improve dosimetry in breast brachytherapy, Medical Physics 35(1): 240-247 (2008).
Shah, NM, et al., The MammoSite Balloon Brachytherapy Catheter for Acderated Partial Breast Irradiation, Semin Radiat. ONcol. Apr. 2005; 15(2); 100-107.

(Continued)

*Primary Examiner* — Michael Kahelin
*Assistant Examiner* — Joshua D Lannu
(74) *Attorney, Agent, or Firm* — Stan Collier, Esq.

(57) ABSTRACT

A radiation modulator is used with a low energy source for breast brachytherapy using a balloon-like catheter. The clinical evaluation of the patient determines the modulator's optimal configuration so as to produce a non-uniform dose distribution to avoid healthy tissue. This modulation may range from a few percent to many tens of percent. A modulating member having predetermined dimensions and materials, i.e., length, width, thickness, is attached to a catheter in close proximity to the intended location of the radioactive source. The modulating member, for example, may be shaped as a rectangular plate, an oval plate or such and be attachable to a catheter.

13 Claims, 7 Drawing Sheets

OTHER PUBLICATIONS

Wazer De,. et al., "Clinically evident fat necrosis in women treated with high-dose-rate brachytherapy alone for early-stage breast cancer," Int J. Radiat. ONcol. Biol. Phys. May 1, 2001; 50(1); 107-111.

"National Surgical Adjuvant Breast and Bowel Project", NSABP Protocol B-39-RTOG Protocol 0413, Mar. 13, 2007, (cover and index only).

* cited by examiner

| Parameter | Range | Increment | Comment |
|---|---|---|---|
| Modulator Thickness | 0.00 mm to 0.20 mm | 0.02 mm | Representing attenuation of more than a factor of 2. |
| Modulator Angular Extent | 0° to 180° | 15° | |
| Modulator Angular Extent | 1.0 mm to 5.0 mm | 0.5 mm | Representing ~25% of the source length to ~120% of the source length |

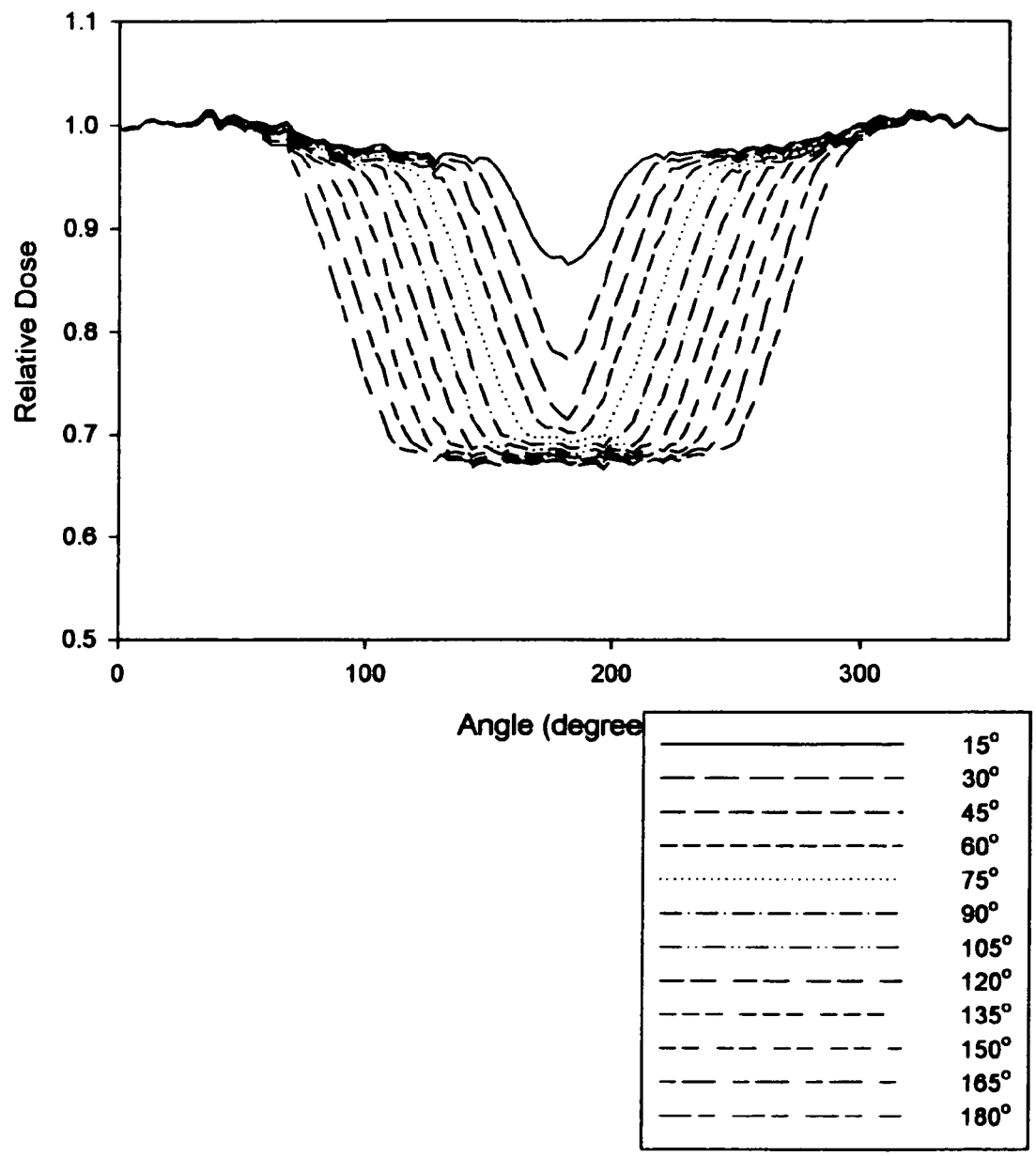

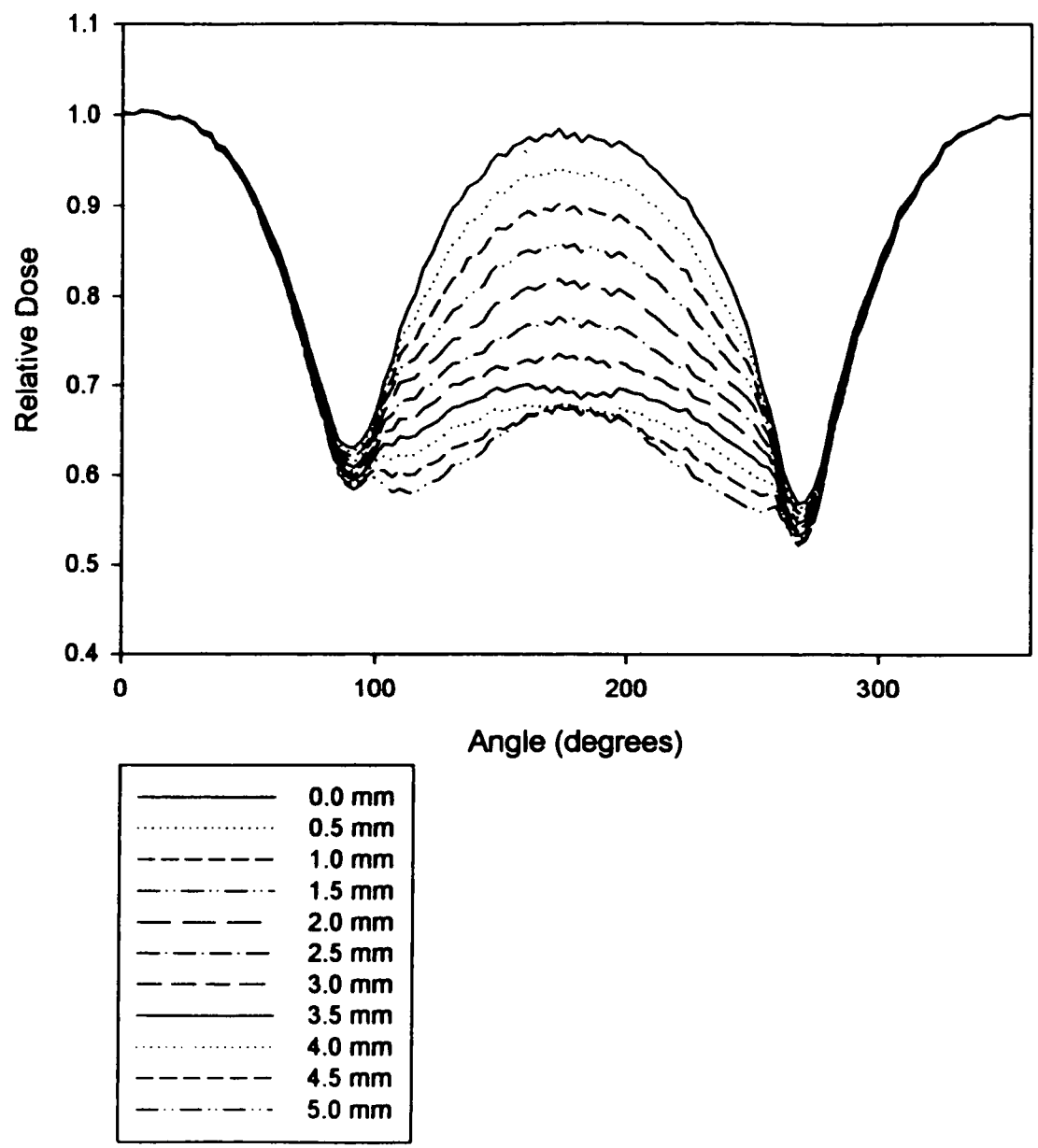

DEVICE AND METHOD FOR INTENSITY MODULATED BRACHYTHERAPY

CROSS REFERENCES TO RELATED APPLICATIONS

NA

REFERENCE TO FEDERALLY SPONSORED RESEARCH OR DEVELOPMENT

This patent application resulted from research supported by an Award Number R43CA134036 from the National Cancer Institute. The contents is solely the responsibility of the inventor/author and does not necessarily represent the official views of the National Cancer Institute or the National Institutes of Health.

REFERENCE TO JOINT RESEARCH AGREEMENTS

NA

REFERENCE TO SEQUENCE LISTING

NA

BACKGROUND OF THE INVENTION

1. Field of the Invention

The present invention relates generally to medical treatment of cancerous tissue, and, in particular, relates to the medical treatment of cancerous tissue by use of radiation, and, in greater particularity, relates to medical treatment of cancerous breast tissue by a source of radiation using brachytherapy.

2. Description of the Prior Art

Various techniques have been developed to treat tumors in the body. In general, the use of radiation as a means to reduce or eliminate malignancy has been known for many years. One of the major issues in all of the techniques is the prevention of damage to healthy tissue.

The type of radiation treatment of malignant tumors most often performed involves directing a beam of radiation from a point external to the patient's body onto the area of the body in which the tumor is located, for the purpose of shrinking and ultimately destroying the tumor. This technique is known as "teletherapy" or external beam radiation therapy. Such treatment exposes normal healthy tissue to the high dosage of radiation in the beam and consequently subjects the normal tissue to potential injury.

In contrast to external beam radiation therapy, brachytherapy is a method of radiation treatment of cancerous tissue in which the radiation source is placed in or near the cancerous tissue. Brachytherapy treatment permits administration of a higher radiation dose to the tumor with better sparing of surrounding normal healthy tissues.

Brachytherapy came into use as a treatment tool for cancer soon after the discovery of radium by Marie Curie in 1898. Goldberg and London used it for the treatment of facial basal cell carcinomas in 1903 with surface applicators.

Brachytherapy can be applied to cancer either by permanent implantation or by temporary application of removable sources. A variety of radionuclides and methods for permanent implantation have been developed.

Permanent implantation results in the radioactive sources, or seeds, being left in the body in perpetuity, delivering their radiation dose until the radioactive material in the source has completely decayed away. This is not desirable in many cases.

Temporary brachytherapy is a process whereby the radioactive sources are placed into the body, usually using an applicator, such as a needle, catheter or other tubular apparatus, for a period of time to deliver the requisite radiation dose, and then the sources are removed. With this treatment modality, applicators are prepositioned in the patient. The sources are later temporarily placed within them. This procedure is known in the field as "afterloading."

Originally, temporary brachytherapy was performed using a technique that became known as "Low Dose Rate Brachytherapy." Using this technique, radioactive sources would be applied to provide a dose rate of 0.4 to 2 Gy/hour to the tumor. Using these techniques, treatment would take several days, during which period the patient would remain hospitalized. Low dose rate techniques utilized a variety of radioactive isotopes, including $^{125}$Iodine, $^{137}$Cesium, $^{198}$Gold and $^{192}$Iridium.

Later, a technique for "High Dose Rate Brachytherapy" was developed. In current practice, this high dose rate brachytherapy technique uses a source to provide dose rates in the range of 2-7 Gy/minute. This technique permitted the treatment to be performed in less than an hour, and without the hospitalization of the patient. These treatments are typically delivered in multiple fractions over several days or weeks.

This high dose rate brachytherapy method generally employs a highly radioactive source integrally attached to a driving cable, which together are known as a source assembly. This source assembly is typically delivered via a catheter or other applicator appliance through a natural cavity, duct or vessel of the body directly to the tumor site for localized irradiation. An alternative approach is to insert a closed-end needle directly into the tissue to be irradiated to create the channel for source delivery. This technique is less likely to expose normal healthy tissue to injury than if external beam radiation were used. One or more catheters, for example, may be implanted in the patient's body to provide a path from an external point to and through the tumor site, so that the interior of the tumor mass is accessible via the catheter(s). The radioactive source is then mechanically delivered by pushing the source by means of the attached driving cable through the catheter for localized irradiation of the tumor for a very short period of time, usually in the range of only a few minutes per treatment.

The high dose rate source is securely located at the end of the source assembly, the other end of which is attached to a controllable apparatus known as a remote afterloader, for advancement or retraction. Advancement of the source assembly through the catheter to the proper locations for treatment of the tumor is achieved by pushing on the driving cable portion of the source assembly by an electro-mechanical device (afterloader). The source is left in the selected positions for predetermined time intervals (programmed into the afterloader) deemed necessary to provide the desired treatment, and is then automatically retracted and returned to a shielded storage area within the afterloader.

The radiation from a brachytherapy source is emitted nearly isotropically from the source, i.e., of equal intensity in all directions. This is disadvantageous in certain circumstances where the source may be located near to critical normal tissue which needs to be spared from the radiation. A number of techniques have been presented to provide shielding around a portion of the radiation source to occlude, absorb, the radiation being emitted in unwanted directions.

One patent describes a x-ray source with moveable local shielding positioned to direct x-rays from the source through the x-ray transparent window to the selected site. This describes a shielding element to occlude a portion of the radiation emitted from the source, essentially leaving the radiation unobstructed in other directions.

Another patent discloses a radiation source upon a push rod that is inserted into a delivery lumen of a shaft. A radiation shielding component is situated near the radiation source to block radiation and is configured to allow radiation therefrom in a predetermined pattern. The shielding component may be composed of a metal or a radiation absorbing material of different density. The device may be used to treat tissue surrounding a body cavity or an intracorporeal site and would include a cavity filling member into which the radiation source with shielding is inserted for treatment. The radiation shielding may be tubular or partially tubular or be imbedded into the wall of the catheter. The radiation shield may be solid or liquid in nature. A further related patent discloses a shielding member being tubular in design and centered upon the radiation source. A window in the tubular structure allows the radiation to exit without shielding. The window has a predetermined shape so as to treat diseased tissues.

One patent application publication describes a directionally emitting radioactive source for brachytherapy wherein a shielding element occludes a portion of the radiation emitted from the source, essentially leaving the radiation unobstructed in other directions. A variation in the radiation dose is noted due to the limited ability to totally block the radiation by the shielding.

Several other patents disclose treating vessels such as arteries in the vascular system. Non-circular dose patterns are produced by an attenuator section having two semi-circular components or bands, tubular sections, placed together, wherein one subtends an angle of about 200 degrees and the other about 120 degrees.

Another patent discloses the treatment of a prostate through the urethra with a radiation source having metal tubular shielding. The urethra/prostate are dilated to move the urethra to a lower dose position. Multiple sleeves of different lengths, thicknesses, and materials can be used to adjust the dose patterns to lessen damage to tissue adjacent the prostate and the urethra.

Accordingly, there is an established need for a device for modulating radiation from a brachytherapy source for treating breast cancer, in particular.

SUMMARY OF THE INVENTION

The present invention is directed at a device for adjusting the dose distribution from a low energy radioactive source within a balloon-like catheter for use in breast brachytherapy.

The present invention is a radiation modulator for use with a low energy source for breast brachytherapy using a balloon-like catheter. The clinical evaluation of the patient determines the modulator's optimal configuration so as to produce a non-uniform dose distribution. This modulation may range from a few percent to many tens of percent. In particular, this modulation can adjust the range to a predetermined value from less than about 95% to greater than 1%, or from 75% to greater than 10%. This is particularly important in breast brachytherapy since the development of Accelerated Partial Breast Irradiation (APBI) procedure performed with, for example, the MammoSite® balloon applicator of Hologic, Inc. The modulator of the present invention is better able to adjust the dose distribution to conform to the patient's relevant anatomy thus allowing more patients to be treated which would not have been possible before. One or more modulating members having predetermined dimensions and materials, i.e., length, width, thickness, etc., is attached to a catheter in close proximity to the intended location of the radioactive source. The one or more modulating member(s), for example, may be shaped as a rectangular plate, an oval or circular plate, a stripe, or such and be attachable to a catheter.

The use of the modulating breast applicator in conjunction with a $^{169}$Ytterbium source can sufficiently modulate the intensity in cases where the skin separation is less than optimum. Such a modulating applicator can permit MammoSite® brachytherapy to be performed in cases where the skin surface is closer than the currently recommended limits. Perhaps more importantly, such an applicator could be more widely used to limit the dose to the skin in cases where the skin surface is within these acceptable limits (7-10 mm) in order to reduce the probability of skin toxicity. Such a development could reduce the occurrence of fibrosis, telangiectasias, and atrophic dermatitis to patients being treated with MammoSite® brachytherapy.

An embodiment of the present invention is to provide means for breast brachytherapy.

It is another embodiment of the present invention to provide to provide a modulator that is used with a balloon-like catheter.

It is a further embodiment of the present invention to provide a modulator for use with low energy radioactive sources used in breast brachytherapy.

It is still a further embodiment of the present invention to provide a modulator able to be configured to a patient's critical anatomy for breast brachytherapy.

It is yet a further embodiment of the present invention to provide a modulator for use in breast brachytherapy using available devices and procedures such as provided by the MammoSite® device and procedure.

It is yet a further desire of the embodiments of the present invention to reduce the radiation dose to reduce toxicity to the skin.

It is yet a further desire of the embodiments of the present invention to benefit many patients for whom MammoSite® brachytherapy is not currently an option because of the proximity of the skin (or chest wall) to the balloon surface, and/or further benefit patients who would currently be MammoSite® brachytherapy candidates by reducing their skin dose, and thereby reducing the probability of toxicity.

These and other embodiments, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 7 is a graphical representation of doses versus angular extent; and

FIG. 8 is a graphical representation of doses versus axial extent.

Like reference numerals refer to like parts throughout the several views of the drawings.

DETAILED DESCRIPTION OF THE PREFERRED EMBODIMENTS

The present invention is directed at a radiation modulating applicator for use in breast brachytherapy using, in particular, low energy radioactive sources.

Figure 1:
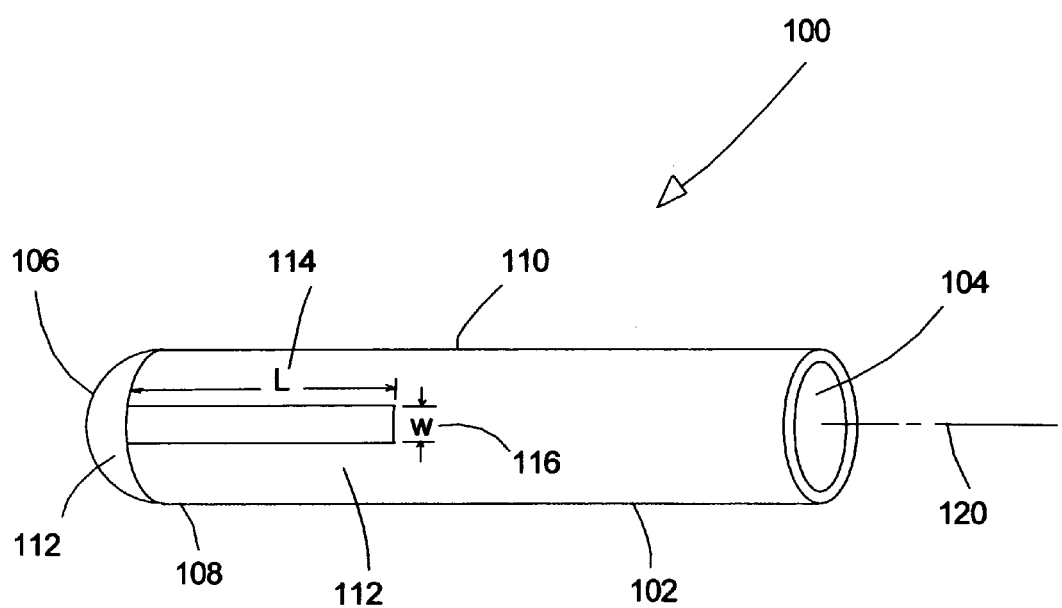
FIG. 1 is a side perspective view of a modulating applicator of a preferred embodiment of the present invention.
Figure 1:
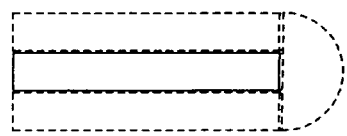

Turning to the drawings, wherein like components are designated by like reference numerals throughout the various figures, attention is initially directed to FIG. 1 which illustrates a side perspective view of the modulating applicator or device 100 constructed according to the present invention.

As best shown in FIG. 1, the modulating applicator 100 has a cylindrical body 102 which has an enclosure or lumen 104. A cap 106 is attached to the distal end 108. The cylindrical body 102 has an outer surface 110 and upon that outer surface 110 is affixed one or more modulating member(s) 112. The modulating member 112 has a predetermined length 114 and a predetermined width 116 and a predetermined depth 118, not shown, being formed of a material whose thickness determines the amount of a particular radiation, for example, $^{169}$Ytterbium, to pass therethrough so that the 100% isodose line, for example, is located approximately at the skin when the breast is compressed by the balloon of the MammoSite® applicator. It should be understood that the one or more modulating members 112 may have any shape or be composed of a material that is based upon the radiation source, the patient's anatomy and a desired treatment. Further, the modulating member 112 provides a unique dose distribution that is a function of the shape of the radiation source, the type of the radiation source, and also the subtended angle relative to a central axis 120 as will be further discussed herein. See outlined modulating members in FIG. 1.

Figure 2:
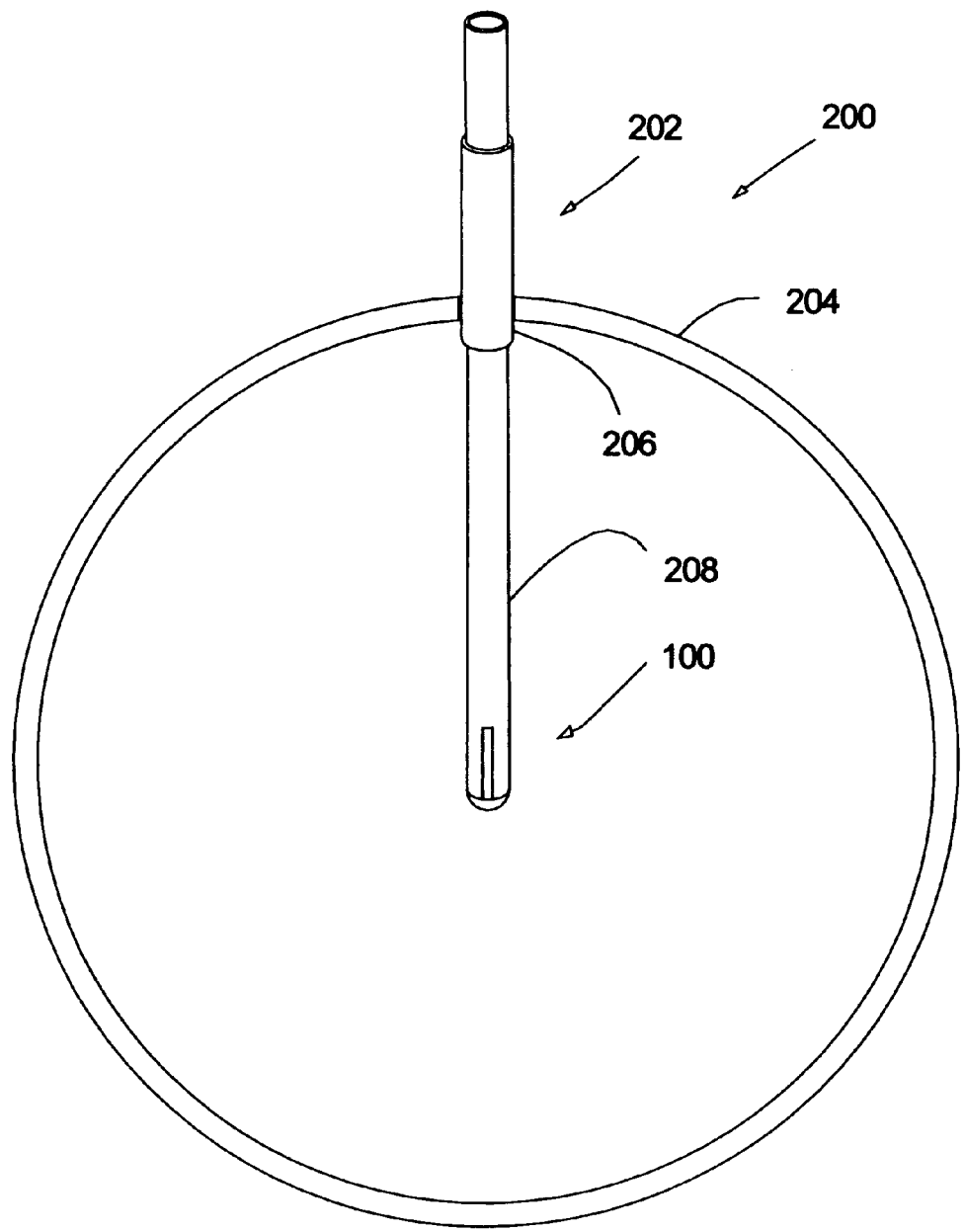
FIG. 2 is a side perspective view of the modulating applicator of the present invention of FIG. 1 being one embodiment of a catheter being used with a MammoSite® applicator.

The present invention may be used in a method employing a MammoSite® device 200, only partially shown in FIG. 2, that consists of a single double lumen catheter 202 with an inflatable balloon 204 at a distal tip 206. The balloon 204 is placed in the lumpectomy cavity, not shown, up to 10 weeks after the breast cancer surgery in an outpatient setting and is then filled with saline such that the surrounding tissue is stretched tightly around it. In one procedure, a high dose rate (HDR) brachytherapy source is then inserted through the inner lumen into the center of the balloon, and radiation is delivered to the shell of tissue immediately surrounding the lumpectomy cavity. The use of a single brachytherapy catheter improves patient comfort over the competitive interstitial brachytherapy technique. This device ostensibly provides a relatively simple and less practitioner-dependent delivery method for APBI. Treatment with the MammoSite® catheter is designed to be an outpatient procedure, and the device can be removed in the clinic after the final fraction.

The dosimetric characteristics of MammoSite® device are not ideal since the anatomy of each patient is different. Skin dose with the MammoSite® device can be quite high because any portion of the skin that falls within 1 cm of the balloon surface will be exposed to the full prescription dose or more. This high skin dose is reason for concern. Among patients treated with external-beam irradiation, fibrosis, telangiectasias, and atrophic dermatitis are common late consequences of the high skin doses.

Because of concerns about radiosensitivity of the skin, the American Brachytherapy Society has recommended that the maximum skin dose be limited to less than 145% of the prescription dose, typically to a limited area. Similarly, the criteria of the NSABP B-39/RTOG 0413 Phase III Clinical Trial for MammoSite® APBI specifies:

"Minimal balloon surface-skin distance—Ideally, the minimal balloon surface-skin distance should be $\geq$7 mm. However, if the balloon-skin thickness is 5 mm to 7 mm, then it will be considered acceptable for treatment after appropriate treatment planning documents that the maximum skin dose at any point is $\leq$145% of prescription dose, assuring that the skin dose does not exceed acceptable limits."

Although adoption of APBI using $^{192}$Iridium and a MammoSite® Applicator is growing, a significant number of lumpectomy patients are not candidates for this treatment because the skin surface is too close to the balloon. Similar concerns exist for the dose to the chest wall.

Thus, in one embodiment of the present invention it is desired to thus modulate the intensity distribution around the MammoSite® balloon in order to generate dose distributions that better conform to the patient anatomy. Because of the feasibility of modulating the photons from relatively low-energy sources with relatively thin amounts of highly absorbing material (such as gold), conformal dose distributions can be achieved that will extend the use of this MammoSite® technique to many more patients.

For example, the use of a modulating breast applicator in conjunction with a currently FDA-cleared $^{169}$Ytterbium source can sufficiently modulate the intensity in cases where the skin separation is less than optimum. Such a modulating applicator 100 can permit MammoSite® brachytherapy to be performed in cases where the skin surface is closer than the currently recommended limits. Perhaps more importantly, the modulating applicator 100 could be more widely used to limit the dose to the skin in cases where the skin surface is within these acceptable limits (7-10 mm) in order to reduce the probability of skin toxicity. Such a development could reduce the occurrence of fibrosis, telangiectasias, and atrophic dermatitis to patients being treated with MammoSite® brachytherapy.

A secondary clinical benefit to this technique may result from reduction of the very high dose in close proximity to the balloon surface. A report by Wazer et al. found that incidence of fat necrosis to be statistically related to the volume of tissue receiving fractional doses of 150% and 200% of the prescription dose. Their results suggest that reduction in the volume of breast tissue receiving the highest doses would reduce the likely incidence of fat necrosis. Fat necrosis has been observed in several series of MammoSite patients. The reduction of the very high dose in the region adjacent to the balloon surface in the direction of the modulating member 112, while maintaining this dose well above the prescription dose, would further reduce the volume of tissue subjected to these high doses, and therefore may provide some clinical benefit in the reduction of fat necrosis toxicity.

The present invention will benefit many patients for whom MammoSite® brachytherapy is not currently an option because of the proximity of the skin (or chest wall) to the balloon surface. This will also benefit patients who would currently be MammoSite® brachytherapy candidates by reducing their skin dose, and thereby reducing the probability of toxicity.

As an example, the use of a $^{169}$Ytterbium source in conjunction with the modulating breast applicator 100 will sufficiently modulate the intensity in the treatment volume around the MammoSite® balloon to result in dose distributions which better conform to the patient anatomy. In particular, in cases where the skin surface was less than 10 mm from the surface of the balloon (within the treatment volume) the modulating applicator 100 can reduce the dose at the skin surface to 100% of the prescription dose, thereby permitting MammoSite® brachytherapy to be used in cases where the skin surface is closer than the currently-recommended limits.

A Monte Carlo study of the modulating applicator 100 assumed the skin surface was located only 7 mm from the surface of the balloon with the purpose of limiting the dose at this location to only 100% of the prescription dose.

Figure 3:
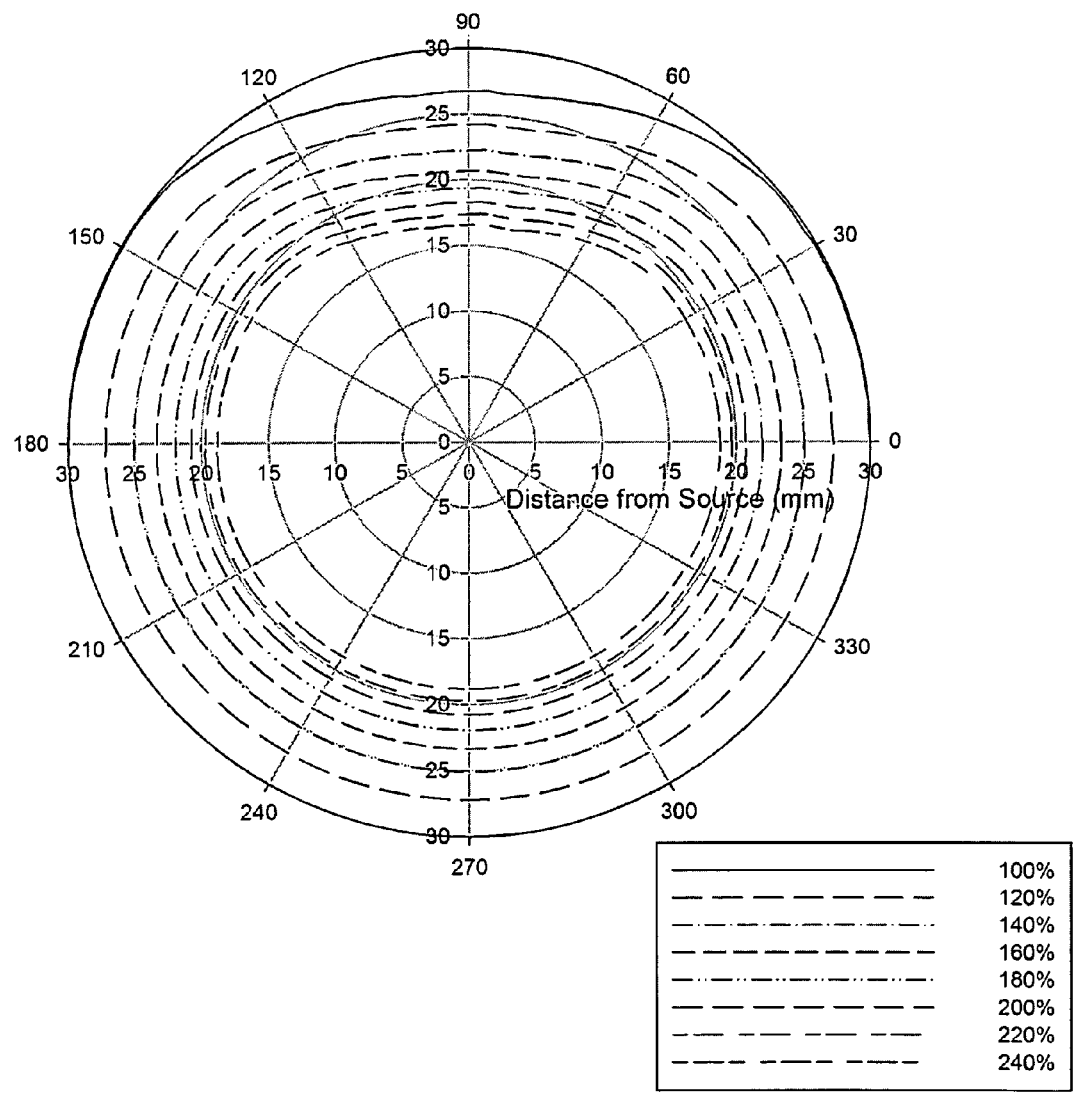
FIG. 3 is a graphical representation of a Monte Carlo simulation of the dose distribution showing isodose contours around the perpendicular bisector of a $^{169}$Ytterbium source using the MCNP5 code and a F6 Tally.

The postulated carrier/catheter 208 has embedded within its outer surface 110 a gold foil of 70 microns (0.07 mm) thickness with a length equivalent to the length of the $^{169}$Ytterbium source and extending over an angular range of 60°. The gold foil may range in thickness from about 0.01 to about 0.50 mm, and also have an angular range from 5 to 180 degrees. The test results show that the use of this very thin (0.07 mm or 70 micron) gold modulating member can modulate the dose distribution sufficiently to locate the 100% isodose line to conform to the skin when located only 7 mm from the balloon surface. See FIG. 3, for example, being the isodose contours resulting from a Monte Carlo simulation of the dose distribution around the perpendicular bisector a $^{169}$Ytterbium source located in the carrier/catheter with an axial extent equal to the length of the active source. See FIGS. 1, 2 and 4.

To illustrate the effects of modulator thickness, modulator angular extent, and modulator axial extent, a series of Monte Carlo simulations were generated. These represent a complex matrix of interdependent parameters. For example, due to scattered dose from unmodulated directions, the intensity-modulating effect of a given thickness of material may differ at different distances from the source/modulator (i.e., closer to the modulator, the scattered intensity from around the modulator may be lower than it would be further away from the modulator). Similarly, also due to scatter, the intensity-modulating effect of the angular extent of the modulator may differ as a function of distance from the source/modulator. (i.e., the penumbra may be sharper near to the modulator and broader at greater distances from the modulator due to scatter within the balloon and target tissue.)

This evaluation used detailed Monte Carlo simulations to calculate three-dimensional dose distributions through the treatment volume. The Monte Carlo simulations were designed to independently assess the effect of each parameter. The specific strategy for each parameter is described below.

Monte Carlo radiation transport calculations were performed on a Windows™ based personal computer running version 1.51 of the MCNP5 Monte Carlo computer code. Input files were designed to simulate geometrical and elemental compositions of the source, applicator and patient. Uniformly distributed $^{169}$Ytterbium photons were generated in the core of a SPEC Model M49 source with photon and secondary electron transport simulated through both the brachytherapy source and surrounding applicator and phantom using default MCPLIB04 photo-atomic cross-section tables supplied with MCNP5. The deposited energy in each scoring voxel was converted to dose. Simulations were performed with the number of photon histories chosen to obtain a Monte Carlo tally precision of less than 1%. All simulations were operated in the photon and electron transport mode (Mode: p,e in the MCNP code) so that both primary photons and resulting secondary electrons are properly transported. $^{169}$Ytterbium's complete photon spectrum was used.

Data was calculated from the output of an MCNP computer model using the MCNP5*FMESH4 tally (MeV cm$^{-2}$), and modified with the DE/DF conversion factors, $v_{en}/\rho$, (cm$^2$ g$^{-1}$) to convert to dose to water in units of MeV g$^{-1}$ photon$^{-1}$.

Monte Carlo Geometry

The Monte Carlo simulation used the SPEC Model M49 source for which TG43 parameters have already been calculated. A source 400, FIG. 4, consists of a solid ytterbium oxide cylinder 402 with a diameter of 0.65 mm and a length of 3.75 mm, with a density of 6.0 mg/mm$^3$ encapsulated in a titanium inner capsule 404 and a stainless steel outer capsule 406.

The capsule 406 is surrounded by a catheter 208 fabricated from plastic in which will be embedded the gold foil modulating member 112.

This entire assembly was contained within a 4.9 mm radius sphere for portability. This source "kernel" was surrounded by the MammoSite® balloon, FIG. 2. The MammoSitee®, balloon is then surrounded by the breast. Since the critical issue is the dose modulation in the vicinity of the skin, the breast is initially postulated as a hemisphere with radius 15 mm larger than the radius of the balloon and concentric with the balloon. This hemisphere will be mounted onto a cylinder with radius equal to the hemisphere radius and with height equal to the radius.

Specific Design Elements

Figures 4, 5:
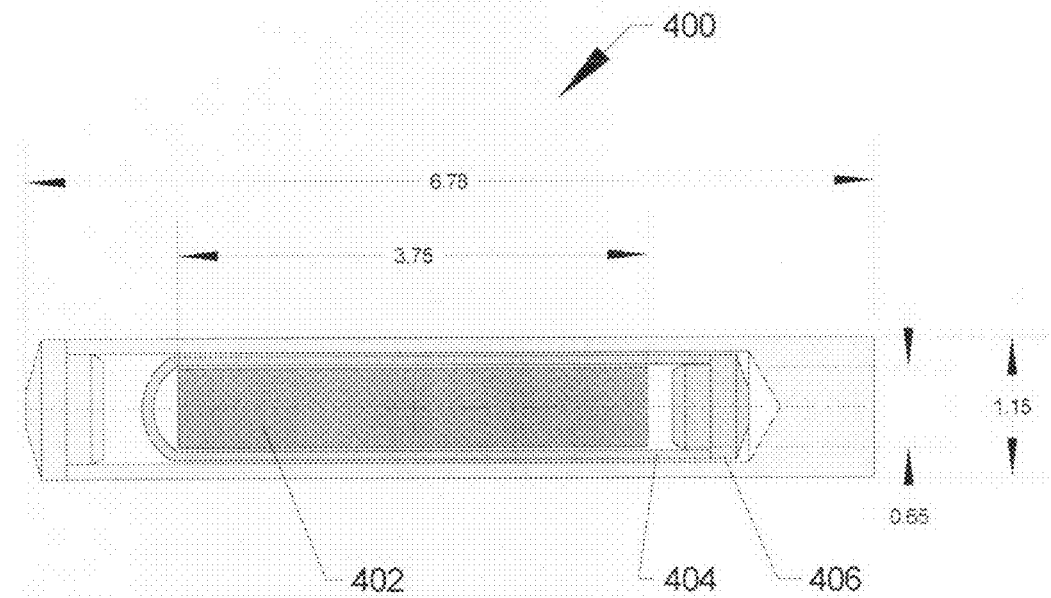
FIG. 4 is a side view of the source used for the graphical representation in FIG. 3.
FIG. 5 is a table giving the parameters used for the modulator in a Monte Carlo simulation.
Figure 6:
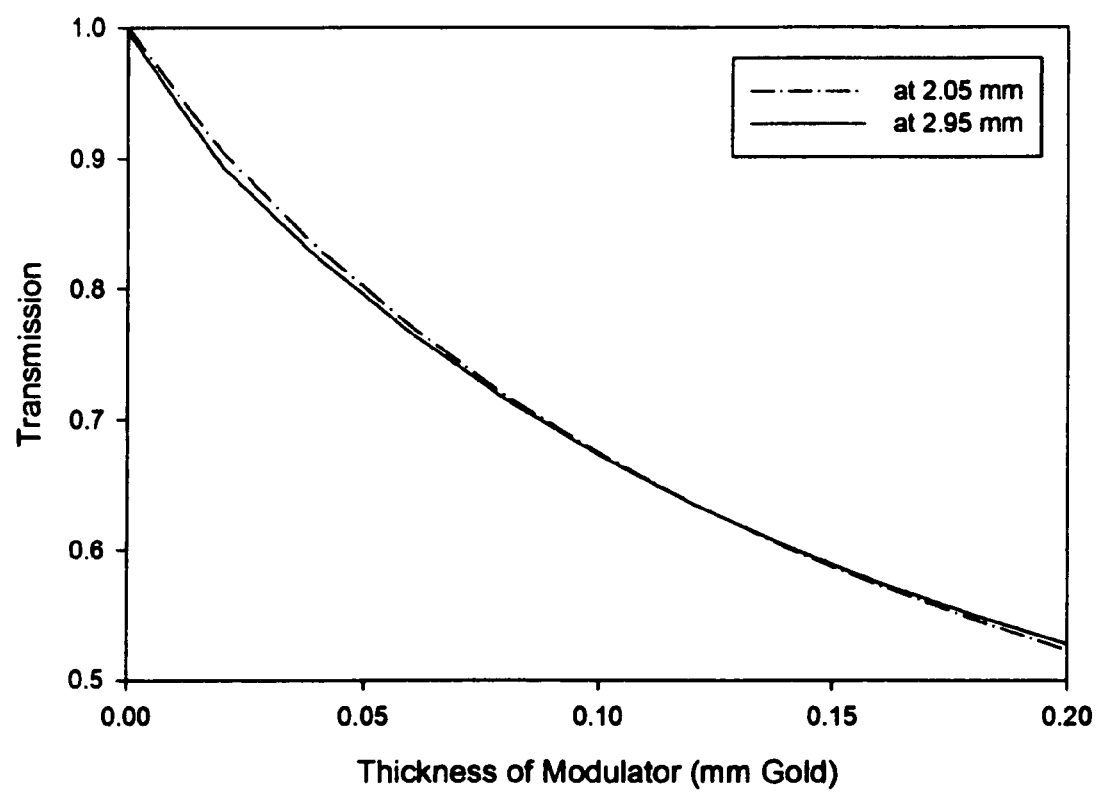
FIG. 6 is a graphical representation of the transmission through a modulator.

The Table in FIG. 5 shows the parameters and ranges to be dosimetrically characterized by Monte Carlo simulation. For this modulator thickness analysis, a Cylindrical Mesh Tally with the mesh axis parallel and collinear to the source axis was used. The modulator covered an angle of 180° and a length of 5.0 mm. The modulator thickness was varied from 0.00 mm thick to 0.20 mm thick in increments of 0.02 mm. The transmission through the modulator was calculated at radial distances from 20.5 mm from the source (just outside the balloon) to 29.5 mm (just inside the prescription point) in 1.0 mm increments. The results of this calculation are shown in FIG. 6. There was very little difference in transmission over the entire range of the prescription volume as is evidenced in FIG. 6, which shows the transmission at the extremes of the range of 20.5 mm to 29.5 mm from the balloon.

Modulator Angular Extent

For this angular extent analysis, the same Cylindrical Mesh Tally with the mesh axis parallel and collinear to the source axis was used. For this analysis, the modulator was 0.10 mm thick (the middle of the range examined) and 5.0 mm long. The modulator angular extent ranged from 0 to 180° in increments of 15°. The dose radially outward from the center of the source was calculated as a function of angular extent over the range of distances from 20.5 mm (just outside the surface of the balloon) to 29.5 mm from the source (just inside the prescription volume) in increments of 1.0 mm (i.e. over the entire prescription volume). FIG. 7 shows the effect of this angular extent at a distance of 29.5 mm from the source.

Modulator Axial Extent

For this axial extent analysis, the same Cylindrical Mesh Tally, however, with the mesh axis perpendicular to the source axis was used. For this analysis, the modulator was 0.10 mm thick (the middle of the range examined) and 180° in angular extent. The modulator was centered on the source and the length ranged from 0.0 to 5.0 mm in increments of 0.5 mm. The dose radially outward from the center of the source was calculated as a function of axial extent over the range of distances from 20.5 mm (just outside the surface of the balloon) to 29.5 mm from the source (just inside the prescription volume) in increments of 1.0 mm (i.e. over the entire prescription volume). FIG. 8 shows the effect of this axial extent at a distance of 29.5 mm from the source.

The following United States patents or patent publications are incorporated by reference: 2005/0261541; U.S. Pat. No. 7,413,539; U.S. Pat. No. 7,407,476; U.S. Pat. No. 6,540,655; U.S. Pat. No. 6,482,142; U.S. Pat. No. 6,6256,816; U.S. Pat. No. 6,077,213; and U.S. Pat. No. 6,036,631.

Since many modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A modulating applicator for use in treating cancerous tissues with radiation, said modulating applicator comprising:
    one or more modulating members, said modulating member being positioned about a radioactive source when inserted into a patient, said modulating member being adapted to reduce radioactive doses to predetermined values to tissues/structures of the patient at given distances from the radioactive source, said modulating member being composed of a radioactive absorbing material, said modulating member having predetermined dimensions to control the isodose distribution based upon clinical assessment of the patient, said modulating member being composed of gold or a similar material having a thickness of about 0.01 to about 0.50 mm, said modulating member having a length substantially equivalent to the length of radioactive source; and
    a catheter, said modulating member being integrally mounted to said catheter in a predetermined position proximally to one end thereof, said catheter having an enclosure into which the radioactive source can be positioned proximal to said modulating member wherein radiation from the radioactive source must partially pass through said modulating member, said modulating member extending over an axial angular extent range about an axis of said catheter from about 5 to 180 degrees, said modulating member being composed of a material that does not shield the radiation from the radioactive source but allows for a predetermined reduction thereof, said catheter being inserted into a patient during treatment, said catheter further having a capped end.

2. The modulating applicator as recited in claim 1, wherein said modulating applicator further includes a low energy radioactive source.

3. The modulating applicator as recited in claim 2, wherein during brachytherapy treatment said low energy radioactive source comprises wave-emitting radiation.

4. The modulating applicator as recited in claim 3, wherein during brachytherapy said low energy radioactive source comprises photon radiation from $^{169}$Ytterbium or similar radioactive materials.

5. The modulating applicator as defined in claim 1, wherein said predetermined values are less than about 95% and greater than about 1%.

6. The modulating applicator as defined in claim 5, wherein said predetermined values are less than about 75% and greater than about 10%.

7. The modulating applicator as defined in claim 1, wherein the thickness is about 0.05 to about 0.25 mm.

8. The modulating applicator as defined in claim 1, wherein the axial angular extent (FIG. 7) range is about 15 to about 175 degrees.

9. A method of performing brachytherapy, said method comprising the steps of:
    performing a clinical analysis of a patient and the patient's anatomy requiring brachytherapy;
    determining a radioactive source for treatment;
    determining a modulating applicator for use with the radioactive source and for applying the radiation to the patient's anatomy to maximize the effects of brachytherapy and to minimize damage to the patient's anatomy, wherein said modulating applicator comprises:
        one or more modulating members, said modulating member being positioned about a radioactive source when inserted into a patient, said modulating member being adapted to reduce radioactive doses to predetermined values to tissues/structures of the patient at given distances from the radioactive source, said modulating member being composed of a radioactive absorbing material, said modulating member having predetermined dimensions to control the isodose distribution based upon clinical assessment of the patient, said modulating member being composed of gold or a similar material having a thickness of about 0.01 to about 0.50 mm, said modulating member having a length substantially equivalent to the length of radioactive source; and
        a catheter, said modulating member being integrally mounted to said catheter in a predetermined position proximally to one end thereof, said catheter having an enclosure into which the radioactive source can be positioned proximal to said modulating member wherein radiation from the radioactive source must partially pass through said modulating member, said modulating member extending over an axial angular range about an axis of said catheter from about 5 to 180 degrees, said modulating member
        being composed of a material that does not shield the radiation from the radioactive source but allows for a predetermined reduction thereof, said catheter being inserted into a patient during treatment, said catheter further having a capped end;
    positioning the modulating applicator in the patient;
    inserting the radioactive source into the modulating applicator;
    allowing for a treatment time; and
    removing the radioactive source and the modulating applicator after the treatment time.

10. The method as defined in claim 9, wherein the brachytherapy uses a low energy radioactive source within the modulating applicator.

11. The method as defined in claim 10, wherein the brachytherapy uses a low energy radioactive source comprising photon radiation from $^{169}$Ytterbium or similar radioactive materials.

12. The method as defined in claim 11, wherein a balloon-like device is adapted to be placed within the body cavity or intracorporeal site, said balloon-like device having a tubular device for accessing an interior of the balloon-like device, said modulating applicator being insertable into the tubular device, said radioactive source being insertable into said catheter of said modulating applicator for treatment, said modulating applicator being positioned near a center of the balloon-like device and only in contact at an entry point.

13. The method as defined in claim 9, wherein the breast brachytherapy uses an accelerated partial breast irradiation (APBI) technique.

* * * * *